United States Patent [19]

Hayashi et al.

[11] Patent Number: 5,081,015
[45] Date of Patent: Jan. 14, 1992

[54] ENZYME ELECTRODE AND METHOD FOR DETERMINATION OF ALCOHOL CONTENT USING THE SAME

[75] Inventors: Ryuzo Hayashi, Higashiosaka; Akio Kariyone, Kyoto; Yoshio Hashizume, Kakogawa, all of Japan

[73] Assignee: Kanzaki Paper Mfg. Co., Ltd., Tokyo, Japan

[21] Appl. No.: 401,132

[22] Filed: Aug. 30, 1989

[30] Foreign Application Priority Data

Aug. 30, 1988 [JP] Japan .................. 63-217641
Aug. 31, 1988 [JP] Japan .................. 63-218844

[51] Int. Cl.$^5$ .................................................. C12Q 1/54
[52] U.S. Cl. ........................................ 435/14; 435/177; 435/817; 435/921; 435/938; 204/403
[58] Field of Search ............... 435/817, 25, 34, 190, 435/921, 938, 14, 4, 177; 204/403

[56] References Cited

U.S. PATENT DOCUMENTS

| | | | |
|---|---|---|---|
| 4,240,889 | 12/1980 | Yoda et al. ........... | 204/195 B |
| 4,250,261 | 2/1981 | Eggeling et al. ....... | 435/190 |
| 4,430,427 | 2/1984 | Hopkins ............... | 435/25 |
| 4,446,231 | 5/1984 | Self .................. | 435/7 |
| 4,540,668 | 9/1985 | Hopkins ............... | 435/190 |
| 4,556,635 | 12/1985 | Hitzman et al. ........ | 435/25 |
| 4,610,963 | 9/1986 | Matsui et al. ......... | 435/189 |
| 4,810,633 | 3/1989 | Bauer et al. .......... | 435/25 |
| 4,812,398 | 3/1989 | Kondo et al. .......... | 435/14 |
| 4,900,666 | 2/1990 | Phillips .............. | 435/25 |
| 4,971,901 | 11/1990 | Hayashi et al. ........ | 435/176 |

FOREIGN PATENT DOCUMENTS 60-176587 9/1985 Japan .
62-215387 9/1987 Japan .

OTHER PUBLICATIONS

Guibaullt et al., Amperometic Enzyme Electrodes, Analytica Chimica Acta, 69 (1974) pp. 189-194.

*Primary Examiner*—David L. Lacey
*Assistant Examiner*—Janelle D. Waack
*Attorney, Agent, or Firm*—Wenderoth, Lind & Ponack

[57] ABSTRACT

An enzyme electrode possessing an immobilized enzyme membrane or an immobilized enzyme layer composed by applying a solution containing alcohol oxidase and a crosslinking agent, in which the solution further contains reduced glutathione.

According to the invention it is possible to immobilize alcohol oxidase stably, and an excellent immobilized enzyme electrode for alcohol measurement is obtained. Furthermore, by this invention, a highly sensitive and stable measuring method is conducted quite easily.

18 Claims, 4 Drawing Sheets

ENZYME ELECTRODE AND METHOD FOR DETERMINATION OF ALCOHOL CONTENT USING THE SAME

BACKGROUND OF THE INVENTION

1. Field of the Invention

The present invention relates to a highly sensitive and stable enzyme electrode for use in the determination of alcohol content, and moreover to a method for the determination of alcohol content having high accuracy and high sensitivity.

2. Description of the Prior Art

Measuring instruments employing immobilized enzyme working electrodes are known for their handiness, rapidity, substrate specificity and other features, and are extending their applications in wide fields including clinical analysis, food analysis and environmental measurements. Among others, the instrument for amperometric measurement, that is, the instrument designed to detect the increase or decrease of electrode active substance caused by the enzyme reaction as the changes in the current output from the working electrode to which a constant voltage is applied, is easy to enhance the sensitivity and is excellent in stability. Accordingly, various electrodes, instruments and methods using the apparatus for amperometric measurement have been developed.

As a representative method of amperometric method, the measuring method by oxygen electrode and the measuring method by hydrogen peroxide electrode are known. These two methods are most widely employed in the immobilized enzyme electrodes, and the hydrogen peroxide electrode method is superior to the oxygen electrode method in response speed and S/N ratio.

In such situation, in the fields of food, fermentation and clinical analysis, there are keen demands for the development of method and apparatus for determination of alcohol, especially ethanol, and various proposals have been disclosed so far. For example, according to the U.S. Pat. No. 4,556,635, it is proposed to use an enzyme electrode obtained by immobilizing alcohol oxidase, in the determination of alcohol content in a water insoluble solvent. However, the activity of alcohol oxidase which is used in the enzyme electrode for alcohol determination and is an enzyme for catalyzing the oxidation of ethanol is relatively low, and its stability is not sufficient practically.

For example, in the initial research examples, by using alcohol oxidase without immobilizing because the activity of alcohol oxidase is low, a method of detecting the catalytic reaction of the enzyme in the solution by an enzyme electrode was proposed (G. G. Guilbault, G. J. Lubrano: Anal. Chim. Acta, 69, 189, 1974). What is interesting in this report is that it is stated that it is hard to detect in the hydrogen peroxide electrode although it is supposed to produce hydrogen peroxide estimating from the reaction mechanism of alcohol oxidase. In this regard, nothing has been reported in detail yet.

Afterwards, the immobilizing method of alcohol oxidase was improved, and the immobilized enzyme electrodes obtained by immobilizing alcohol oxidase have been reported. Such reports include proposal of a method of immobilizing alcohol oxidase by a mild reaction. Inactivation of alcohol oxidase is prevented as far as possible by coexistence of a polymer more likely to react with crosslinking agent, such as glutaraldehyde, rather than with alcohol oxidase, or a method of using a polymer which is made insoluble by pH changes (Japanese Laid-open Patents No. 60-176587, No. 62-215387). These methods are effective to a certain degree to prevent inactivation of alcohol oxidase, but are weak in the bonding force of alcohol oxidase, and involve a possibility of leakage of alcohol oxidase. Hence they are not a sufficient immobilizing method of alcohol oxidase. Besides, these methods are not by nature enough to solve the fundamental problems, that is, the low activity of alcohol oxidase, in particular, the low activity for producing hydrogen peroxide as mentioned above and the lack of stability of immobilized alcohol oxidase.

Yet, these methods could not improve the thermal stability of enzyme electrode obtained by immobilizing alcohol oxidase. The thermal stability is often used as the index of stability of an enzyme, and the enzyme to be used in enzyme electrode should be preferably high in thermal stability as far as possible. If the enzyme is unstable thermally, it is possible to operate the enzyme electrode at low temperature, but at low temperature the enzyme activity is lowered, and it is likely that the sensitivity be lowered. Moreover, control of temperature of the instrument near room temperature is susceptible to fluctuations of room temperature, and it is relatively difficult. Therefore it is desired that the enzyme electrode may operate stably at a temperature about 10° C. or more higher than room temperature. Alcohol oxidase is however, generally inferior in thermal stability, and it is difficult to operate the enzyme electrode using alcohol oxidase stable at such temperature.

SUMMARY OF THE INVENTION

It is hence a first object of the invention to present an enzyme electrode which is obtained by stably and firmly immobilizing alcohol oxidase.

It is a second object of the invention to present a method for determining alcohol content by using the same enzyme electrode and detecting oxygen.

It is a third object of the invention to present a method for sensitive and stable measurement of alcohol content by using the enzyme electrode and detecting hydrogen peroxide.

It is a fourth object of the invention to present a method for sensitive and stable measurement of alcohol content using the enzyme electrode, by improving the thermal stability of the enzyme electrode obtained by immobilizing alcohol oxidase.

To achieve the first object, the invention presents an enzyme electrode possessing an immobilized enzyme membrane or an immobilized enzyme layer prepared by applying an alcohol oxidase solution containing alcohol oxidase and a crosslinking agent, wherein the solution further contains a reduced glutathione.

In a preferred embodiment, the concentration of the reduced glutathione in the solution is 0.1 mM or more and 10 mM or less.

In other preferred embodiment, the alcohol oxidase to be used is derived from methanol-utilizing microorganism, and more desirably the alcohol oxidase should be derived from Candida yeast or Pichia yeast.

In a different preferred embodiment, the crosslinking agent is a multifunctional aldehyde, and more desirably the multifunctional aldehyde is glutaraldehyde.

In other different preferred embodiment, the concentration of multifunctional aldehyde in the alcohol oxidase solution is 0.1 wt. % or more and 1.0 wt. % or less.

In a further preferred embodiment, the solution contains at least one type of protein aside from alcohol oxidase, and more desirably contains protein of relatively low molecular weight and high amino group content, that is, at least one type selected from gelatin, albumin, globulin, polylysine and polyarginine. Preferably, the weight of the protein is 1/10 or more and 10 times or less of the weight of alcohol oxidase.

To achieve the second object, the invention presents a method for determination of alcohol content characterized by detection of consumed oxygen at the time of oxidation of alcohol, by using the enzyme electrode as described above.

To achieve the third object, the invention presents a method for determination of alcohol content characterized by detection of hydrogen peroxide produced at the time of oxidation of alcohol, by using the enzyme electrode as described above.

Furthermore, to achieve the third object, the invention presents a method for measurement characterized by using an enzyme electrode in buffer solution containing sodium azide, when measuring by detecting the produced hydrogen peroxide, and said enzyme electrode is obtained by immobilizing alcohol oxidase by covalent bond using crosslinking agent.

In a preferred embodiment, the concentration of sodium azide in the buffer solution used in the measurement is 0.1 $\mu$M or more and 1 mM or less.

Furthermore, to achieve the fourth object, the invention presents a method for measurement using an enzyme electrode characterized by addition of polyacrylic acid to a buffer solution in which the enzyme electrode is immersed during the measurement, and the enzyme electrode is obtained by immobilizing alcohol oxidase by covalent bond using a crosslinking agent.

In a preferred embodiment, the concentration of the polyacrylic acid to be added is in a range of 0.001 wt. % to 0.5 wt. %.

This alcohol oxidase is an enzyme produced by basidiomycete, yeast, etc., and it is known to exist particularly abundantly in peroxisome of methanol-utilizing microorganism. The present inventors investigated the characteristics of alcohol oxidase, and attempted various methods of immobilization and measurement, and reached the completion of the invention.

In the first place, in order to prepare a rigid immobilized enzyme membrane as far as possible, aldehydes were used as the crosslinking agent, and it was attempted to immobilize by covalent bond of aldehydes and alcohol oxidase. Alcohol oxidase is a comparatively large enzyme with the molecular weight exceeding 300,000, and it is found that the bonding force is weak in immobilization by covalent bond. The reason is presumed that only a few amino groups of alcohol oxidase to be bonded with aldehyde, for example glutaraldehyde, are exposed on the molecular surface, although alcohol oxidase has a comparatively large molecular weight, or that there are only a small number of amino acids having amino groups capable of bond formation.

Therefore, in order to immobilize alcohol oxidase rigidly, it is necessary to raise the concentration of the crosslinking agent. But when such a measure is taken, the enzyme activity drops suddenly, that is, the enzyme is inactivated.

To prevent such inactivation, the present inventors investigated the stability by using various additives such as dithiothreitol, cysteine, and reduced glutathione. As a result, glutathione is found to be matched with this purpose, and it is also found that an immobilized enzyme membrane excellent in strength is obtained. The reason of prevention of inactivation of alcohol oxidase by the use of reduced glutathione is not clearly known, but the following mechanism is known. Intrinsically, alcohol oxidase is inactivated by copper ion or mercury ion, and it is presumed that the thiol group in the alcohol oxidase molecule takes part in the enzyme reaction. Therefore, during crosslinking reaction by aldehydes it is highly possible that the thiol group which is in the active site of the molecule of alcohol oxidase reacts with aldehyde to be inactivated. However, by coexistence with reduced glutathione which is a oligopeptide possessing thiol residue, it is considered that the thiol group in the molecule of alcohol oxidase is protected so that the inactivation is prevented.

The quantity of addition of reduced glutathione in the alcohol oxidase solution is preferably in a range of 0.1 mM to 10 mM. If the concentration is too low, enough effect is not expected, and if too high, the immobilization is impeded. The reason seems that the free amino group in the molecule of reduced glutathione reacts with aldehyde to lower the concentration of effective aldehyde.

As the alcohol oxidase, the enzymes derived from methanol-utilizing microorganism (methanol-utilizing yeast, methanol-utilizing bacteria, etc.), especially methanol-utilizing Candida yeast and methanol-utilizing Pichia yeast are preferable from the aspect of activity retaining property. Alcohol oxidase is contained abundantly in the peroxisome (microbody) of methanol-utilizing microorganism., For immobilization of alcohol oxidase using aldehyde, it is desired to heat over the room temperature in order to raise the reaction rate and to form a rigid crosslinking film. However, the enzyme derived from basidiomycete may be inactivated when heated over 25° C. However, the enzyme derived from methanol-utilizing microorganism relatively excels in heat resistance, and can withstand about 40° C. if only for a short time.

In particular, from the viewpoint of heat resistance, the enzymes derived from methanol-utilizing Candida yeast and methanol-utilizing Pichia yeast are excellent.

As the crosslinking agent, aldehydes are used, for example, formaldehyde, glyoxal, and glutaraldehyde, and particularly glutaraldehyde is preferably used because the activity lowering is less.

The concentration of aldehyde in the alcohol oxidase solution containing alcohol oxidase is preferably 0.1 wt. % or more and 1.0 wt. % or less, and more preferably 0.2 wt. % or more and 0.7 wt. % or less. If the aldehyde concentration is too low, the strength of the immobilized enzyme membrane is lowered, and if too high, lowering of the activity cannot be prevented sufficiently even if the reduced glutathione is added.

Furthermore, by coexistence of at least one type of protein, aside, from alcohol oxidase, at the time of reaction with crosslinking agent, aforesaid proteins penetrate into gaps of large alcohol oxidase molecules, thereby forming more rigid membranes of immobilized enzyme. To achieve this object, it is desired to use protein relatively low in molecular weight and high in the amino group content. For example, gelatine, albumin, globulin, polylysine, and polyarginine conform to these conditions, and in particular gelatine and albumin are preferable in the aspect of price. These protein get into gaps of large molecules of alcohol oxidase, and are bonded with many multifunctional aldehydes of the crosslinking agent on the molecular surface of the proteins, which is considered to cause to increase the number of crosslinking points of multifunctional aldehyde and alcohol oxidase. The weight of the protein to be added at the time of immobilization is practically preferable from 1/10 to about 10 times the amount of alcohol oxidase by weight. If this content is too small, there is no effect, and if too much, the alcohol oxidase is diluted, and the sensitivity is lowered.

Alcohol oxidase may be directly immobilized on the electrode of platinum of other conductive material, or may be immobilized on a permselective membrane such as formed permeating hydrogen peroxide selectively for removing obstacles such as ascorbic acid.

As the permselective membranes, a various kinds of membranes, for example, a crosslinked membrane of albumin and glutaraldehyde, an acetylcellulose membrane and the like, are used.

The enzyme electrode prepared in this way is not only high in activity when conforming to the method of detecting the consumption of oxygen (oxygen electrode) but also high in activity when detecting hydrogen peroxide (hydrogen peroxide electrode) to use the method as described below. That is to say, in previous method the activity may not be always sufficient when detecting hydrogen peroxide. The present inventors, in order to see this reason, attempted to measured hydrogen peroxide, instead of alcohol, and found that the detecting sensitivity of hydrogen peroxide of the electrode is low. Furthermore, by investigating into the activity of the alcohol oxidase specimen to decompose hydrogen peroxide, an obvious hydrogen peroxide decomposing activity, that is catalase activity was recognized. This is because a hard-to-refine catalase is contained in the alcohol oxidase. Therefore, in order to obtain an excellent hydrogen peroxide electrode, it is preferable to suppress only the catalase activity. To suppress the catalase activity, it is effective to use cyan ion or azide and the like, but, the cyan ion is not desired owing to its toxicity.

Accordingly, sodium azide was added to a buffer solution, in which the solution enzyme reaction was performed. As a result, the catalase activity was evidently lowered, but the alcohol oxidase activity was also lowered. Disturbance of activities of catalase and alcohol oxidase came to be observed when about 0.01 mM of sodium azide was added to the reaction system, and about 5 to 10% of alcohol oxidase activity was reduced when about 0.1 mM was added.

On the other hand, in the enzyme electrode which have immobilized enzyme by covalent bond, a remarkable improvement of resistance to azide ions of alcohol oxidase was noted, and the alcohol oxidase activity is hardly suppressed while it is found that the catalase activity is effectively inhibited.

To the buffer solution used in measurement using enzyme electrode, for example, 100 mM, pH 7.5 sodium phosphate buffer solution, when sodium azide of 0.1 $\mu$M or more and 1 mM or less is added, only the catalase activity can be suppressed. If the sodium azide concentration is too low, the catalase activity cannot be suppressed sufficiently, or if too high, the alcohol oxidase activity is also impeded.

Meanwhile, when an enzyme electrode or an immobilized enzyme membrane is dipped in a buffer solution containing azide ion in higher concentration, for example, a buffer solution containing sodium azide of 100 mM, and is let stand overnight at about 4° C., and is returned into a buffer solution free of sodium azide and let stand for about 5 hours at room temperature, the catalase activity is lost, and the alcohol oxidase activity is recovered about 70%. This is considered because the resistance of catalase to azide is not changed so much although the resistance of alcohol oxidase to azide is increased by immobilization. However, since this method is too time-consuming it is practically desired to always add sodium azide at low concentration to the measuring system.

In addition, the following experiment was conducted in order to enhance the heat resistance of the enzyme electrode having immobilized alcohol oxidase. For example, alcohol oxidase of *Candida boidinii* which is a methanol-utilizing yeast is explained. In order to check the heat resistance of this enzyme, in the first place, reaction of the solution system was conducted. The enzyme was dissolved in 100 mM sodium phosphate buffer solution (pH 7.5), and a specific amount of ethanol, and a solution containing horseradish.peroxidase (hereinafter referred to POD), phenol and 4-aminoantipyrine were added, and a reaction was conducted at 30° C. for a specific time. In this system; ethanol was oxidized into acetaldehyde by the reaction of alcohol oxidase, and hydrogen peroxide was produced at the same time. The produced hydrogen peroxide was immediately decomposed by POD, and a red pigment is produced at this time by phenol and 4-aminoantypirine. The amount of this red pigment was proportional to the produced quantity of hydrogen peroxide, i.e. proportional the oxidized amount of ethanol, and by measuring the absorbance of the reaction solution around 500 nm, the activity of the alcohol oxidase can be known. In this way, the initial enzyme activity was measured. And then only the enzyme solutions were held at 35° C., 37° C., 39° C., 41° C., 43° C., and 45° C. for 30 minutes respectively, and the enzyme activity of each solution was measured again at 30° C. As a result, there was no significant change in the activity up to 37° C., but at 39° C., the activity was lowered to 70% of the initial activity, and at 41° C., to 30%, and at 45° C. the activity was lost almost completely.

Next, alcohol oxidase and bovine serum albumin were mixed by a ratio of 1:1 by weight, and dissolved in a buffer solution, and glutaraldehyde was added by 0.5% by weight, and the mixed solution was applied on a polished platinum electrode, and was allowed to be dried and solidified. Using this electrode as the working electrode, a platinum plate of 1 cm square was used as the counter electrode, and a saturated calomel electrode (hereinafter referred to SCE) was used as the reference electrode, and they were dipped in a 100 mM sodium phosphate buffer solution controlled at a temperature of 30° C., and a voltage of 0.6 V against the SCE was applied to the working electrode by using a potentiostat. In this system, a specific amount of ethanol was added, and the oxidation current of the hydrogen peroxide was recorded. Exchanging the buffer solution, the temperature of the system was elevated at the same step as the solution system, and by letting stand for 30 minutes after the system reached each temperature, similar recording was conducted. In this case, along with the temperature rise, not only the enzyme activity but also the sensitivity of the electrode to hydrogen peroxide varies, and therefore the temperature goes up to a higher temperature than the example of the solution enzyme above, but at 41° C., the activity was similarly lowered to 50% of the initial sensitivity.

Adding 0.1 wt. % of polyacrylic acid to the buffer solution, a newly prepared enzyme electrode was repeatedly measured, and the initial sensitivity could be maintained up to 43° C., and at 45° C., 90% of the initial sensitivity was retained.

Now returning to the measurement of the solution system, when experimented by using a buffer solution adding 0.1 wt. % of polyacrylic acid, the heat resistance was not improved.

Thus, in the immobilized alcohol oxidase, by adding polyacrylic acid to the buffer solution used in measurement, the stability of the enzyme can be enhanced.

The effect by addition of polyacrylic acid in this invention as described herein is a novel phenomenon observed only in the immobilized enzyme system. This polyacrylic acid effect is obtained, of course, in the immobilized enzyme electrode prepared by applying the alcohol oxidase solution containing reduced glutathione. Polyacrylic acid to be added in the buffer solution is preferably about a mean molecular weight of 10,000 to 1,000,000, and the concentration is preferably within a range of 0.001 wt. % to 0.5 wt. %. If the concentration is less than 0.001 wt. %, sufficient effect is not noted, or if too high, the sensitivity may be lowered. The sensitivity drop at high concentration of polyacrylic acid is considered to be due to the impediment of diffusion of the substrate due to elevation of solution viscosity, or lowering of the activity of the enzyme itself.

The reason of stabilizing effect of polyacrylic acid on immobilized alcohol oxidase system is not clearly known. It is anyway presumed that certain changes occur in the conformation of alcohol oxidase by immobilization to encourage interaction with polyacrylic acid, thereby becoming stable thermally in a form of alcohol oxidase-polyacrylic acid complex.

BRIEF DESCRIPTION OF THE DRAWINGS

These and other objects of the invention, as well as the features and advantages thereof, will be better understood and appreciated from the following detailed description taken in conjunction with the drawings, in which.

DETAILED DESCRIPTION OF THE PREFERRED EMBODIMENTS

Figure 1:
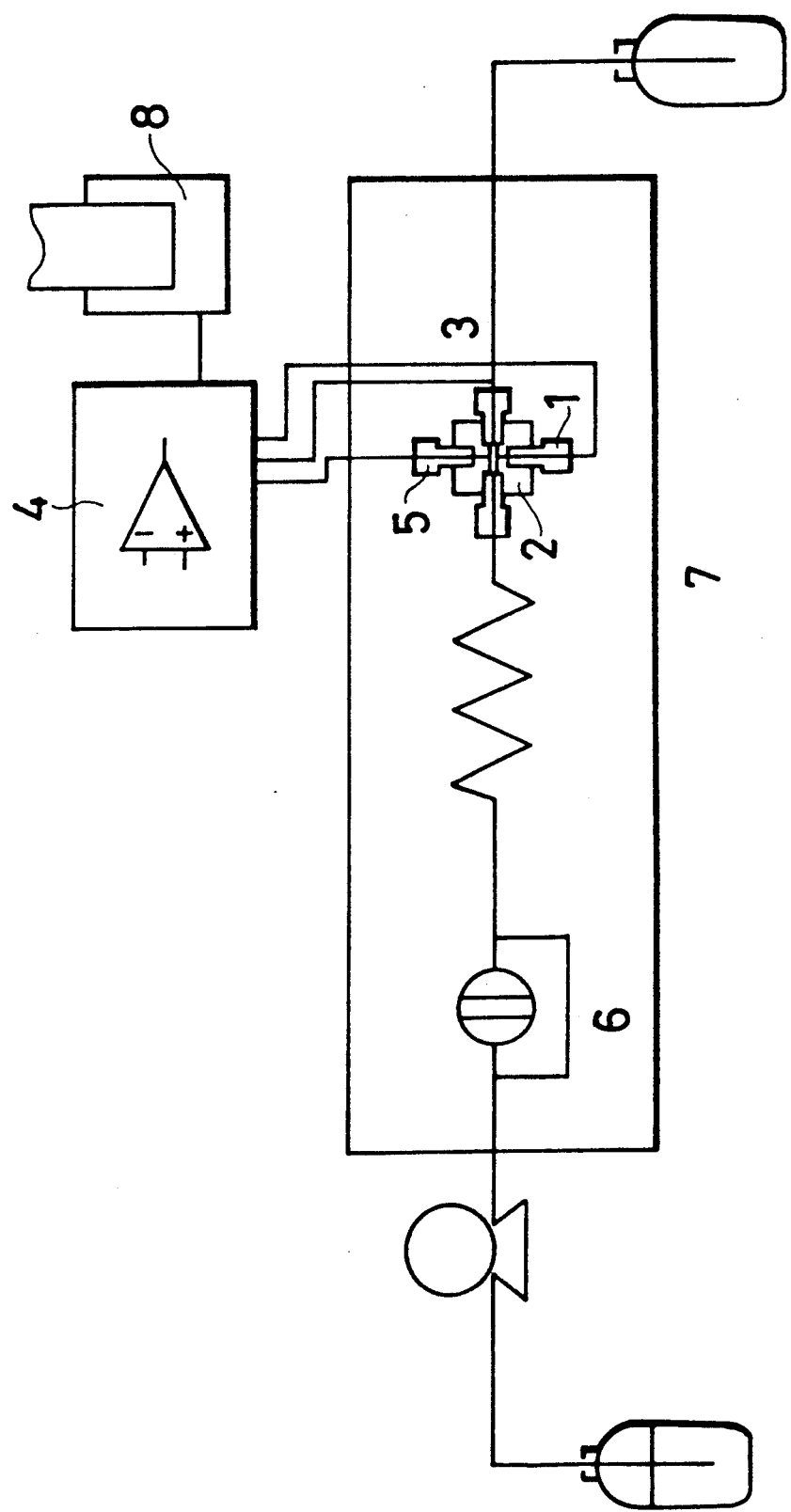
FIG. 1 shows a flow type measuring instrument used in individual embodiments.

Referring now to the drawings, some of the preferred embodiments of the invention are described in details below. The invention, however, is not limited to these embodiments alone. In the following description, % denotes wt. %.

EXAMPLE 1

(1) Preparation of electrode

The side surface of a platinum wire of 2 mm in diameter was coated with a heat-shrinkable Teflon, and one end of the wire was finished smoothly by using a file and an emery paper of 1500 count. Using this platinum wire as the working electrode, and a 1 cm square platinum plate as the counter electrode, and a saturated calomel electrode (SCE) as the reference electrode, an electrolysis was conducted in 0.1M sulfuric acid, at +1.4 V, for 10 minutes. Then the platinum wire was washed well in water, was dried for 10 minutes at 40° C., and was dipped for 1 hour in an anhydrous toluene solution containing 10% γ-aminopropyl triethoxy silane, and washed. An enzyme was immobilized on this amino-silane platinum wire in the following manner.

5 mg of alcohol oxidase (Sigma Co.; derived from *Candida boidinii*) and 5 mg of bovine serum albumin (Sigma Co.; Fraction V) were dissolved in 1 ml of 100 mM sodium phosphate buffer solution (pH 7.5), and 1 mM of reduced glutathione and 0.5% of glutaraldehyde were added. This mixture solution was promptly put on a prepared platinum wire, and was dried and cured at 40° C. for 30 minutes. Afterwards, the product was stored in 100 mM sodium phosphate buffer solution (pH 7.5).

(2) Measuring method

Using a prepared enzyme electrode as the working electrode, a 1 cm square platinum plate electrode as the counter electrode, and a SCE as the reference electrode, they were connected to a potentiostat. A voltage of 0.6 V against the SCE was applied to the working electrode, and the measuring system was composed. The buffer solution used in measurement was 100 mM sodium phosphate buffer solution (pH 7.5) containing 50 mM potassium chloride. The measuring temperature was 30° C. (±0.2° C.). While stirring the solution by a magnetic stirrer, ethanol was added into the system by 1 mM each, and the increase of the current output was recorded in the recorder.

Plotting a calibration curve for 1 to 10 mM of ethanol, the sensitivity of the electrode per 1 mM of ethanol was determined from the slope of the calibration curve. The sensitivity of 20 electrodes prepared separately was measured, and the mean and standard deviation were calculated (Table 1). It is thus found that the electrodes obtained by above described method are stable and high in sensitivity.

REFERENCE 1

(1) Preparation of electrode

The electrodes were prepared in the same manner as in Example 1, except that the reduced glutathione was not used when producing the electrodes.

(2) Measuring method

Measured in the same manner as in Example 1.

From the slope of the calibration curve, the sensitivity of the electrode per 1 mM of ethanol was determined. By measuring the sensitivity of 20 electrodes prepared separately, the mean and standard deviation are shown in Table 1 and compared with the results of Example 1. Evidently, it is known that the electrodes prepared in this manner have the sensitivity of only one-third that of Example 1. Thus, the effect of addition of reduced glutathione is confirmed.

TABLE 1

| Measuring example | Electrode sensitivity/mean ± standard deviation (μA/mM · ethanol) |
|---|---|
| Example 1 | 0.210 ± 0.011 |
| Reference 1 | 0.072 ± 0.008 |

EXAMPLE 2

(1) Preparation of electrode

Electrodes were prepared in the same manner as in Example 1.

(2) Measuring method

Using a prepared enzyme electrode as the working electrode, a 1 cm square platinum plate electrode as the counter electrode, and an SCE as the reference electrode, they were connected to a potentiostat. Applying a voltage of 0.6 V against the SCE to the working electrode, the measuring system was composed. The buffer solution used in the measurement was 100 mM sodium phosphate buffer solution (pH 7.5) containing 50 mM potassium chloride. The measuring temperature was 30° C. ($\pm 0.2°$ C.). While stirring the solution by a magnetic stirrer, ethanol was added into the system by 1 mM each, and the increase of the current output was recorded in a recorder.

From the slope of the calibration curve, the sensitivity of the electrode per 1 mM of ethanol was determined. Next, the buffer solution for measurement was exchanged with a fresh one, and the solution was continuously stirred for 5 hours, and the sensitivity was measured again. The results are shown in Table 2. As clear from Table 2, by such method of preparation, the sensitivity of the electrode is not changed.

EXAMPLE 3

(1) Preparation of electrode

Electrodes were prepared in the same manner as in Example 1, except that the bovine serum albumin was not used and that 10 mg of alcohol oxidase was used instead of 5 mg of alcohol oxidase.

(2) Measuring method

Measured in the same manner as in Example 2.

From the slope of the calibration curve, the sensitivity of the electrode per 1 mM of ethanol was determined. The buffer solution for measurement was exchanged with a fresh one, and the solution was continuously stirred for 5 hours, and the sensitivity was measured again. The results are shown in Table 2. As known from Table 2, the sensitivity of the electrode prepared in this manner was lowered. By visual observation, separation of the immobilized enzyme membrane was recognized, and it is seen that the strength of the immobilized membrane is slightly inferior if protein other than alcohol oxidase such as albumin is not present.

TABLE 2

| Measuring example | Electrode sensitivity ($\mu$A/mM ethanol) | |
|---|---|---|
| | Upon start of measurement | After 5-hour stirring |
| Example 2 | 0.205 | 0.203 |
| Example 3 | 0.151 | 0.020 |

EXAMPLE 4

(1) Preparation of electrode

Electrodes were prepared in the same manner as in Example 1.

(2) Measuring method

Using a prepared enzyme electrode as the working electrode, a 1 cm square platinum plate electrode as the counter electrode, and an SCE as the reference electrode, they were connected to a potentiostat. And applied a voltage of 0.6 V against the SCE to the working electrode. The buffer solution used in measurement was a 100 mM sodium phosphate buffer solution (pH 7.5) containing 50 mM potassium chloride with 10 $\mu$M sodium azide. The measuring temperature was 30° C. ($\pm 0.2°$ C.). While stirring the solution by a magnetic stirrer, ethanol was added into the system by 1 mM each, and the increase of current output was recorded in a recorder. Similarly, hydrogen peroxide with a known concentration was measured. From the slope of the calibration curve, the sensitivity of the electrode per 1 mM of ethanol or 1 mM of hydrogen peroxide was determined. Measuring the sensitivity of 20 electrodes prepared separately, the mean and standard deviation are shown in Table 3. By such measuring method, the sensitivity of about 5 times as high as in Example 1 was obtained concerning ethanol. Furthermore, compared with the result of Example 5 mentioned below, the sensitivity to hydrogen peroxide is also known to be enhaced. Thus, the effect of addition of sodium azide has been confirmed.

EXAMPLE 5

(1) Preparation of electrode

Electrodes were prepared in the same manner as in Example 1.

(2) Measuring method

Measured in the same manner as in Example 4, except that sodium azide was not added to the buffer solution.

From the slope of the calibration curve, the sensitivity of the electrode per 1 mM of ethanol or 1 mM of hydrogen peroxide was determined. The results are shown in Table3. Evidently, as for both ethanol and hydrogen peroxide, the sensitivity is low as compared with Example 4. This is because hydrogen peroxide is decomposed by catalase.

TABLE 3

| Measuring example | Electrode sensitivity/mean $\pm$ standard deviation ($\mu$A/mM) | |
|---|---|---|
| | Ethanol | Hydrogen peroxide |
| Example 4 | 1.022 $\pm$ 0.050 | 6.150 $\pm$ 0.180 |
| Example 5 | 0.207 $\pm$ 0.010 | 1.170 $\pm$ 0.071 |

EXAMPLE 6

(1) Preparation of electrode

The side surface of a platinum wire of 2 mm in diameter was coated with a heat-shrinkable Teflon, and one end of the wire was smoothly finished by using a file and an emery paper of 1500 count. Using this platinum wire as the working electrode, and a 1 cm square platinum plate as the counter electrode, and a saturated calomel electrode (SEC) as the reference electrode, an electrolysis was conducted for 10 minutes at +1.4 V in 0.1M sulfuric acid. Then the platinum wire was washed well in water, and was dried for 10 minutes at 40° C., and was dipped in anhydrous toluene solution of 10% $\gamma$-amino propyl triethoxy silane for 1 hour, and was washed. On this amino-silane platinum wire, an enzyme was immobilized in the following manner.

5 mg of alcohol oxidase (Sigma Co.; derived from *Candida boidinii*) and 5 mg of bovine serum albumin (Sigma Co.; Fraction V) were dissolved in 1 ml of 100 mM sodium phosphate buffer solution (pH 7.5), and 0.5% of glutaraldehyde was added. This mixed solution was promptly put on a prepared platinum wire by 5 μl, and was dried and cured for 30 minutes at 40° C. Then it was stored in 100 mM sodium phosphate buffer solution (pH 7.5).

(2) Measuring method

The prepared enzyme electrode was used at the working electrode and incorporated into a flow type measuring apparatus shown in FIG. 1. Using an Ag|AgCl reference electrode 1 as the reference electrode, a stainless steel pipe connected to a outlet of flow cell 2 was used as the counter electrode 3. These three electrodes were connected to a potentiostat 4. To the working electrode 5, a voltage of 0.6 V against the Ag|AgCl reference electrode was applied. The line after the injection port 6 of the flow type measuring apparatus was put into a thermostat 7. The buffer solution used in the measurement was 100 mM sodium phosphate buffer solution (pH 7.5) containing 50 mM potassium chloride and 0.01% polyacrylic acid.

Initially, the measuring temperature was 30° C. (±0.2° C.). From the injection port 6, 5 μl of 50 mM ethanol aqueous solution was poured, and the current output was recorded in a recorder 8, and the peak current was read.

Figure 2:
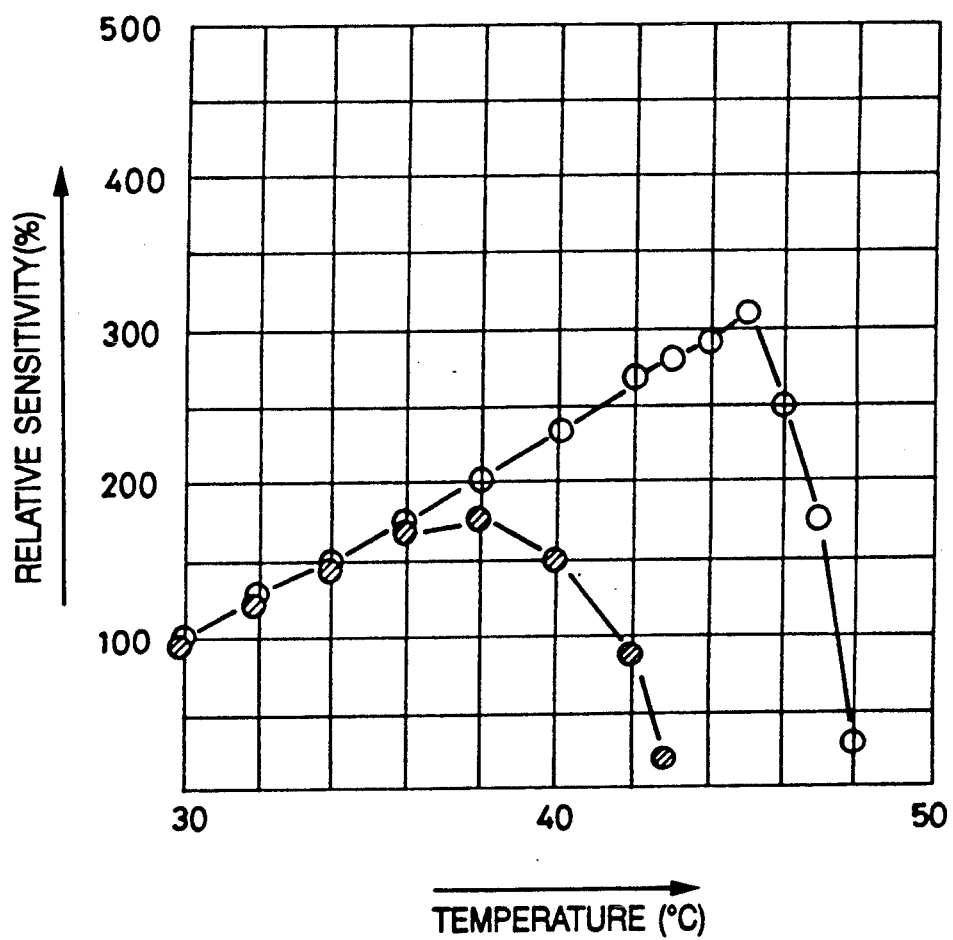
FIG. 2 shows results of measurement of Example 6 (○ mark) and Reference 2 (● mark)

Then the temperature of the thermostat was raised, and ethanol aqueous solution was added every time reaching a specific temperature, and each peak current is shown in FIG. 2 (○ mark), taking the current at 30° C. as 100%. In the presence of polyacrylic acid, the sensitivity was elevated up to about 45° C.

Reference 2

(1) Preparation of electrode

Electrodes were prepared in the same manner as in Example 6.

(2) Measuring method

Measured in the same manner as in Example 6, except that polyacrylic acid was not added to the buffer solution. The results are shown in FIG. 2 (● mark). Obviously, the heat resistance was inferior to Example 6.

EXAMPLE 7

(1) Preparation of electrode

Electrodes were prepared in the same manner as in Example 6.

(2) Measuring method

The same measuring apparatus as in Example 6 was used. Setting the thermostat temperature at 40° C., 5 μl of 50 mM ethanol aqueous solution was injected at specific time intervals, and the peak currents were measured (○ mark in FIG. 3). It is known that the sensitivity was not changed even in 5 hours.

REFERENCE 3

(1) Preparation of electrode

Electrodes were prepared in the same manner as in Example 6.

(2) Method of measurement

Measured in the same manner as in Example 7, except that polyacrylic acid was not added to the buffer solution used in measurement, by using the same measuring apparatus.

Figure 3:
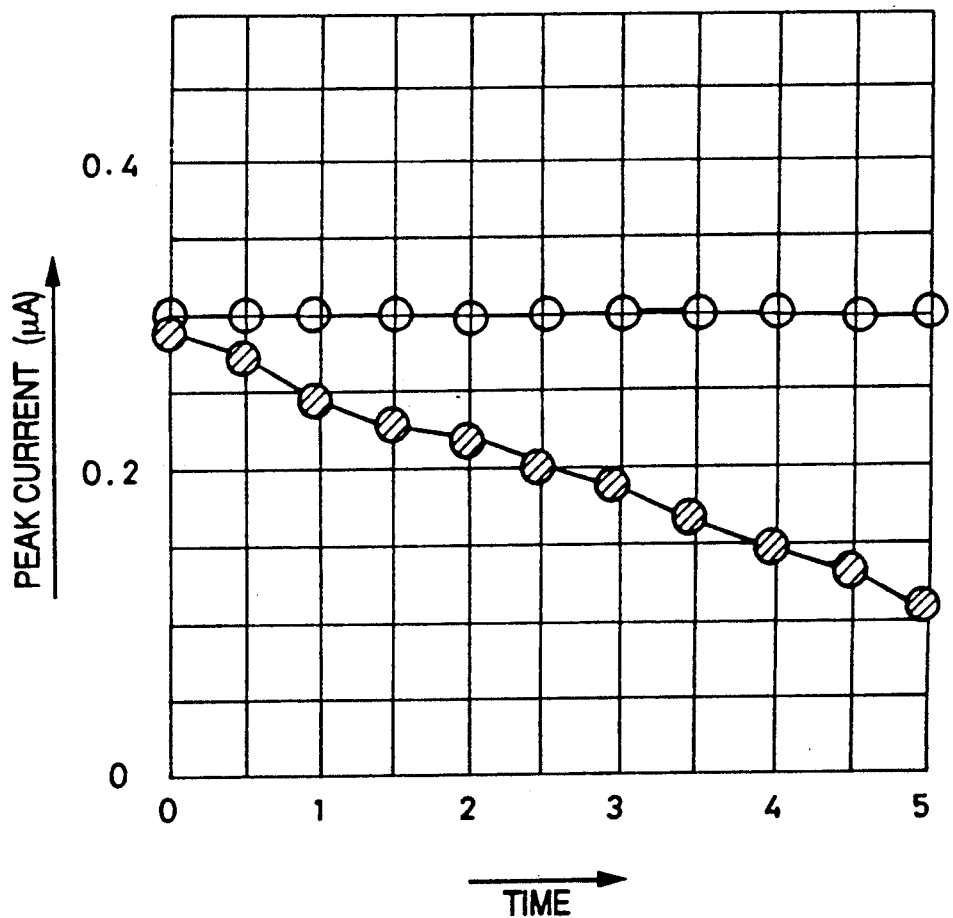
FIG. 3 shows results of measurement of Example 7 (○ mark) and Reference 3 (● mark)

Setting the thermostat temperature at 40° C., 5 μl of 50 mM ethanol aqueous solution was added at specific time intervals, and the peak currents were measured (● mark in FIG. 3). The sensitivity was not stable, and was gradually lowered, and as compared with Example 7, the effect of addition of polyacrylic acid was obviously noted.

EXAMPLE 8

(1) Preparation of electrode

The side surface of a platinum wire of 2 mm in diameter was coated with a heat-shrinkable Teflon, and one end of the wire was smoothly finished by using a file and an emergy paper of 1500 count. Using this platinum wire as the working electrode, a 1 cm square platinum plate as the counter electrode, and a saturated calomel electrode (SCE) as the reference electrode, an electrolysis was conducted for 10 minutes at +1.4 V in 0.1M sulfuric acid. The platinum wire was washed well in water, and was dried for 10 minutes at 40° C., and was dipped in an anhydrous toluene solution of 10% γ-aminopropyl triethoxy silane for 1 hour, and was washed. On this amino-silane platinum wire, an enzyme was immobilized in the following manner.

To 100 μl of alcohol oxidase (Sigma Co.; derived from *Pichia pastolis*, liquid enzyme), 5 mg of bovine serum albumin (Sigma Co.; Fraction V) was added, and 1 ml of 100 mM sodium phosphate buffer solution (pH 7.5) saturated with ammonium sulfate was added in an ice-chilled state. By this operation, the solution became white and turbid, and the enzyme and albumin were made insoluble. This solution was centrifugal separated for 10 minutes at 4° C., 20000×g (g: gravitational acceleration). Removing the supernatant, 100 μl of 100 mM sodium phosphate buffer solution (pH 7.5) was added, and the sedimenting protein was dissolved again. This solution was dialyzed for 1 hour at 4° C. for the same buffer solution as used in the re-dissolving. The solution after dialysis was used in the subsequent immobilizing operation. By the operation up to dialysis, the sugars and glycerol contained as stabilizers in the enzyme specimen and the ammonium sulfate used for precipitating the protein were removed.

To the solution after dialysis, glutaraldehyde was added by 0.2%. This mixed solution was promptly put on a prepared amino-silane platinum wire by 3 μl, and was dried and cured for 15 minutes at 40° C. Afterward, the product was stored in 100 mM sodium phosphate buffer solution (pH 7.5).

(2) Measuring method

Using the prepared enzyme electrode as the working electrode, it was incorporated into a flow type measuring apparatus shown in FIG. 1. As the reference electrode, an Ag|AgCl reference electrode was used, and a stainless steel pipe connected to a flow cell 2 was used as the counter electrode 3. These three electrodes were connected to a potentiostat 4. A voltage of +0.6 V to the Ag|AgCl reference electrode was applied to the working electrode 5. The line after the injection port 6 of the flow type measuring apparatus was assembled in a thermostat 7. The buffer solution used in measurement was 100 mM sodium phosphate buffer solution (pH 7.5) containing 50 mM potassium chloride, 0.01% polyacrylic acid, and 10 μM sodium azide.

Figure 4:
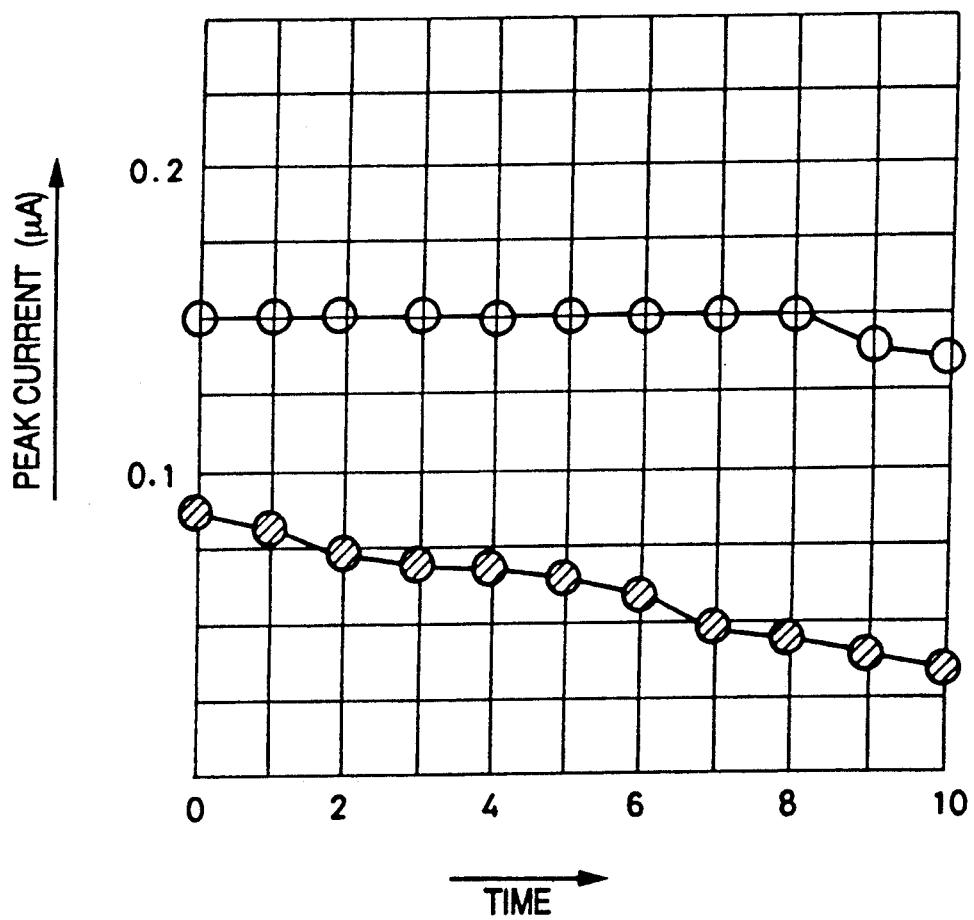
FIG. 4 shows results of measurement of Example 8 (○ mark) and Reference 4 (● mark).

Setting the thermostat temperature at 37° C., 5 μl of 2 mM ethanol aqueous solution was injected at specific time intervals, and the peak current was measured (○ mark in FIG. 4). It is known that the sensitivity is not lowered even in 8 hours.

REFERENCE 4

(1) Preparation of electrode

Electrodes were prepared in the same manner as in Example 8.

(2) Measuring method

Measured in the same manner as in Example 8, except that polyacrylic acid and sodium azide were not added to the phosphate buffer solution used in measurement, using the same measuring instrument.

Setting the thermostat temperature at 37° C., 5 μl of 2 mM ethanol aqueous solution was injected at specific time intervals, and the peak current was measured (● mark) in FIG. 4). In this example, the sensitivity was low, and the sensitivity was not stable, and the sensitivity was gradually lowered. As compared with Example 8, hence, the effects of addition of polyacrylic acid and sodium azide were evidently observed.

EXAMPLE 9

(1) Preparation electrode

Same as in Example 8, a platinum wire was prepared and alcohol oxidase was refined.

To the alcohol oxidase solution after dialysis, 5 mM reduced glutathione was added and 0.2% of glutaraldehyde was added. This mixed solution was promptly put on a prepared amino-silane platinum wire by 3 μl, and was dried and cured at 40° C. for 15 minutes. The electrode was stored in 100 mM sodium phosphate buffer solution (pH 7.5).

(2) Measuring method

Using the prepared enzyme electrode as the working electrode, it was incorporated into a flow type measuring apparatus shown in FIG. 1. As the reference electrode, an Ag|AgCl reference electrode 1 was used, and a stainless steel pipe connected to an outlet of flow cell 2 was used as the counter electrode 3. These three electrodes were connected to a potentiostat. To the working electrode 5, a voltage of +0.6 V against the Ag|AgCl reference electrode was applied. The line after the injection port 6 of the flow type measuring apparatus was assembled in a thermostat 7. The buffer solution used in measurement was 100 mM sodium phosphate buffer solution (pH 7.5) containing 50 mM potassium chloride, 0.01% polyacrylic acid and 10 μM sodium azide.

Setting the thermostat temperature at 37° C., 5 μl of 2 mM ethanol aqueous solution was injected, and the peak current was recorded. In the same time range as in Example 8, similarly, there was no change in the sensitivity. The mean and standard deviation of sensitivity in 8 hours was 0.321 and ±0.009 μA. This result corresponds to about 2.1 times that of Example 8. Thus, by adding reduced glutathione at the time of immobilization, the activity of the immobilized enzyme could be kept high.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An enzyme electrode for amperometric measurement, comprising a conductive base material and an immobilized enzyme membrane or an immobilized enzyme layer, said immobilized enzyme membrane or immobilized enzyme layer comprised of a crosslinked reaction product of an alcohol oxidase solution containing alcohol oxidase, a crosslinking agent and reduced glutathione.

2. An enzyme electrode according to claim 1, wherein the concentration of reduced glutathione in the alcohol oxidase solution is 0.1 mM or more and 10 mM or less.

3. An enzyme electrode according to claim 1, wherein the alcohol oxidase to be used is derived from a methanol-utilizing microorganism.

4. An enzyme electrode according to claim 3, wherein the alcohol oxidase is derived from methanol-utilizing Candida yeast.

5. An enzyme electrode according to claim 3, wherein the alcohol oxidase is derived from methanol-utilizing Pichia yeast.

6. An enzyme electrode according to claim 1, wherein the crosslinking agent is multifunctional aldehyde.

7. An enzyme electrode according to claim 6, wherein the multifunctional aldehyde to be used is glutaraldehyde.

8. An enzyme electrode according to claim 6, wherein the concentration of multifunctional aldehyde in the alcohol oxidase solution is 0.1 wt. % or more and 1.0 wt. % or less.

9. An enzyme electrode according to claim 1, wherein the alcohol oxidase solution further contains at least one type of protein other than alcohol oxidase, and wherein said protein other than alcohol oxidase has a property of increasing the physical strength of said immobilized enzyme membrane or immobilized enzyme layer.

10. An enzyme electrode according to claim 9, wherein the protein other than alcohol oxidase is at least one selected from the group consisting of gelatin, albumin, globulin, polylysine, and polyarginine.

11. An enzyme electrode according to claim 9, wherein the weight of said protein is 1/10 or more of the weight of alcohol oxidase and 10 times or less thereof.

12. A method for determination of alcohol content in a sample comprising the steps of immersing an enzyme electrode in a sample solution, said enzyme electrode comprising a conductive base material and an immobilized enzyme membrane or an immobilized enzyme layer, said immobilized enzyme membrane or immobilized enzyme layer comprised of a crosslinked reaction product of an alcohol oxidase solution containing alcohol oxidase, a crosslinking agent and reduced glutathione, and measuring with said enzyme electrode the amount of oxygen consumed by the oxidation of alcohol catalyzed by said alcohol oxidase.

13. A method for determination of alcohol content in a sample comprising the steps of immersing an enzyme electrode in a sample solution, said enzyme electrode comprising a conductive base material and an immobilized enzyme membrane or an immobilized enzyme layer, said immobilized enzyme membrane or immobilized enzyme layer comprised of a crosslinked reaction product of an alcohol oxidase solution containing alcohol oxidase, a crosslinking agent and reduced glutathione, and measuring with said enzyme electrode the amount of hydrogen peroxide produce by the oxidation of alcohol catalyzed by said alcohol oxidase.

14. A method for determination of alcohol content in a sample by amperometric measurement comprising the steps of immersing an enzyme electrode in a sample solution comprising a buffer solution and sodium azide, said enzyme electrode comprising a conductive base material and an immobilized enzyme membrane or an immobilized enzyme layer, said immobilized enzyme membrane or immobilized enzyme layer comprised of a crosslinked reaction product of an alcohol oxidase solution containing alcohol oxidase, reduced glutathione and a crosslinking agent, and measuring with said enzyme electrode either the amount of oxygen consumed or the amount of hydrogen peroxide produced by the oxidation of alcohol catalyzed by said alcohol oxidase.

15. A method according to claim 14, wherein the concentration of sodium azide in the buffer solution is 0.1 $\mu$M or more and 1 mM or less.

16. A method for determination of alcohol content in a sample by amperometric measurement comprising the steps of immersing an enzyme electrode in a sample solution comprising a buffer solution and polyacrylic acid, said enzyme electrode comprising a conductive base material and an immobilized enzyme membrane or an immobilized enzyme layer, said immobilized enzyme membrane or immobilized enzyme layer comprised of a crosslinked reaction product of an alcohol oxidase solution containing alcohol oxidase, reduced glutathione and a crosslinking agent, and measuring with said enzyme electrode either the amount of oxygen consumed or the amount of hydrogen peroxide produced by the oxidation of alcohol catalyzed by said alcohol oxidase.

17. A method according to claim 16, wherein the concentration of polyacrylic acid to be added is 0.001 wt. % or more and 0.5 wt. % or less.

18. A method for determination of alcohol content in a sample comprising the steps of immersing an enzyme electrode in a sample solution comprising a buffer solution and sodium azide, said enzyme electrode comprising a conductive base material and an immobilized enzyme membrane or an immobilized enzyme layer, said immobilized enzyme membrane or immobilized enzyme layer comprised of a crosslinked reaction product of an alcohol oxidase solution containing alcohol oxidase, a crosslinking agent and reduced glutathione, and measuring with said enzyme electrode the amount of hydrogen peroxide produced by the oxidation of alcohol catalyzed by the alcohol oxidase, wherein the concentration of sodium azide in the buffer solution is 0.1 $\mu$M or more and 1 mM or less.

* * * * *